United States Patent [19]
Bhattacharya

[11] 3,976,197
[45] Aug. 24, 1976

[54] THERMAL CONVECTION COUNTER STREAMING SEDIMENTATION METHOD AND APPARATUS FOR CONTROLLING THE SEX OF MAMMALIAN OFFSPRING

[76] Inventor: Bhairab C. Bhattacharya, 5016 S. 87th St., Omaha, Nebr. 68127

[22] Filed: Nov. 22, 1974

[21] Appl. No.: 526,378

[52] U.S. Cl. .................................. 209/11; 209/158; 209/173; 209/111.7 R; 195/1.8
[51] Int. Cl.² .......................................... B03B 5/00
[58] Field of Search ............ 209/11, 158, 160, 173, 209/208, 209, 1, 111.7; 195/1.8; 128/1 R; 424/85, 105, DIG. 15; 356/208, 201, 203; 331/DIG. 1; 210/96, 94; 235/151.3

[56] References Cited
UNITED STATES PATENTS

| | | | |
|---|---|---|---|
| 1,365,815 | 1/1921 | Charlton | 209/209 |
| 1,917,156 | 7/1933 | Rauschenbusch et al. | 209/160 X |
| 2,379,158 | 6/1945 | Kalischer | 356/208 |
| 2,418,821 | 4/1947 | Coghill et al. | 209/158 |
| 3,315,066 | 4/1967 | Muta et al. | 235/151.3 |
| 3,826,364 | 7/1974 | Bonner et al. | 209/111.7 |
| 3,869,903 | 3/1975 | Beach et al. | 209/160 X |
| 3,901,660 | 8/1975 | Ohorodnik et al. | 209/160 X |

*Primary Examiner*—Frank W. Lutter
*Assistant Examiner*—Ralph J. Hill
*Attorney, Agent, or Firm*—Bacon & Thomas

[57] ABSTRACT

A method and apparatus for controlling the sex of mammalian offspring through separation of X-chromosome female producing sperm and Y-chromosome male producing sperm. The separation is accomplished by producing a thermal convection counter stream within a sedimentation column containing a universal medium with sperm suspended therein, and subsequently allowing the two sperm populations to sediment into different fractions according to different densities. The positive and negative geotaxis thus applied to the sperm facilitate a more efficient separation than has been previously obtained. The apparatus used to accomplish this separation includes means for producing a temperature differential between axial and peripheral portions of the medium contained in the sedimentation column thus creating the necessary thermal convection counter stream, and may also comprise a laser capable of scanning the length of the column and laser detecting means to determine the distribution of sperm produced within the medium.

9 Claims, 2 Drawing Figures

STAGES OF DISTRIBUTION OF MALE AND FEMALE SPERM

THERMAL CONVECTION COUNTER STREAMING SEDIMENTATION METHOD AND APPARATUS FOR CONTROLLING THE SEX OF MAMMALIAN OFFSPRING

CROSS REFERENCE TO RELATED APPLICATIONS

Reference is made to the applications of BHAIRAB CHANDRA BHATTACHARYA, Ser. No. 443,473, filed Mar. 29, 1965 and now abandoned, Ser. No. 873,795, filed Nov. 3, 1969 by the same inventor now U.S. Pat. No. 3,692,897 incorporated herein by reference, and application No. 336,454, filed Feb. 28, 1973 by the same inventor, now U.S. Pat. No. 3,816,249, also incorporated herein by reference.

BACKGROUND OF THE INVENTION

This invention relates to a method and apparatus for controlling the sex of mammalian offspring by separation of X-chromosome female producing sperm of one density from Y-chromosome male producing sperm of a differing density.

As discussed in the aforementioned application, the sex of offspring is controlled by the chromosomes of the particular sperm cell which fertilizes the egg. As further disclosed therein, X-chromosome containing sperm which are responsible for producing female offspring are somewhat more dense than Y-chromosome containing sperm which are responsible for producing male offspring. This difference in density makes possible the separation of sperm into fractions containing substantially all of either the X or the Y sperm. Separation techniques utilizing this density differential are suitable for use with all mammals including human beings and other primates, cattle, swine, sheep, rabbits, cats, goats, horses, donkeys and buffalo. As previously disclosed, mainly in application No. 443,473, the method of separation has been to apply a buoyant force to the sperm to cause the more buoyant sperm to attain a different level in the separation medium than the less buoyant sperm, where the buoyant force applied has been either positive or negative.

It has been noted in the past that the presence of foreign particles in the medium disturbs the buoyant or sedimentation velocity of the sperm as well as the fertilization capacity after separation. The use of the universal medium disclosed in U.S. Pat. No. 3,816,249 substantially eliminates this problem and in addition promotes control of cellular hyperactivity and prolongs sperm life as well. The use of the universal medium as well as the imposition of a low temperature immobilizing the sperm prevents the small difference in density (2 to 5%) between male and female sperm from being neutralized by the high metabolic activity of the sperm.

SUMMARY OF THE INVENTION

In the present invention both positive and negative buoyant forces are used to achieve a more efficient separation of male and female sperm from a mixture of semen and particle free medium held in a vertical sedimentation column under the influence of a thermal convection counter stream at low tempertures.

The present invention is based on the theory that in a closed vessel the molecules contained therein can be influenced to move in two counter streaming courses when a tempurature differential is created between two adjacent areas. In a vertical column of fluid when the peripheral temperature is maintained lower than the axial temperature, a counter stream will be formed moving a peripheral portion of the liquid downwards and the axial portion upwards due to the difference in temperature. The rate of flow of these streams in either direction is dependent on the difference in densities created between the sections. Thus any change in the temperature differential will influence the densities and the rate of flow of the two streams.

If two classes of particles of different density and volume are introduced into a constant counter current stream in a vertical column, the particles will initially be influenced by the velocities of the counter streams; then positive and negative buoyant forces acting on the particles will follow a definite physical law, carrying them apart.

When a small spherical inert particle falls through a medium at rest, it follows Stokes law regarding its sedimentation velocity as influenced by the action on it of the physical forces of buoyancy of the liquid, viscosity of the liquid, gravitational force, and the difference in density between the particles and the medium. For microscopic particles of non-geometrical shape (such as sperm), as a deduction of Stokes law, I have found that:

$$V = \frac{K(\rho - \rho')mg}{3\rho w}$$

where:
 $V$ = particle velocity (cm set$^{-1}$)
 $\rho$ = density of the particles (gm cm$^{-3}$)
 $\rho'$ = density of the medium (gm cm$^{-3}$)
 $m$ = mass of the particle (gm)
 $g$ = acceleration due to gravity (981 cm sec$^{-2}$)
 $w$ = surface attraction due to viscose forces = $\eta.S$
 $K$ = constant for the geometrical form of the particles According to the present invention a thermal convection counter stream is produced within the sedimentation column causing one portion of the medium therein to move at velocity V in an upwards direction and another portion of the medium to move with velocity V in a downwards direction. X-sperm and Y-sperm suspended within the medium will be caused to move at velocities $V_x$ and $V_y$ respectively which velocities will be affected by the velocity of the medium V, the direction of the movement of the medium upwards or downwards, and gravity which will apply a different force on X-sperm particles than on Y-sperm particles according to the differing densities of the two types. As a result of these factors a Y-sperm particle which is less dense than an X-sperm particle tends to rise faster in that portion of the medium moving in an upwards direction and to settle slower in that portion of the medium moving in a downwards direction. Conversely, an X-sperm particle which is more dense tends to rise more slowly than a Y-sperm particle when the medium is moving in an upwards direction and tends to settle more quickly than the Y-sperm particle when the medium is moving in a downwards direction. Over a period of time these circumstances cause the less dense Y-sperm particles to accumulate near the top of the sedimentation column and the more dense X-sperm particles to accumulate near the bottom of the sedimentation column.

Now to give a quantitative description of the phenomena, let us consider a vertical column of fluid in counter-stream flow. In the description below, the following quantities are symbolized:

$V_1$ = velocity of lighter particles
$V_2$ = velocity of heavier particles
X = separation distance between the two classes of particles
$\rho_2$ = density of the heavier particles
$\rho_1$ = density of the lighter particles
$V_T$ = relative velocity of particle with respect to the fluid medium
U = velocity of laminar flow, considered to be directed vertically upwards or downwards
$F_1$ = class density of the lighter particles
$F_2$ = class density of the heavier particles
where:

$$V_T = U - V$$

We assume:
1. that all particles of interest lie in either one of the two uniformly moving masses of fluid,
2. the boundary layer effect near the particle surface is small compared to the fluid volume and hence negligible.

Now in this counter-stream laminar flow let us consider the two types of particles as having densities $\rho_1$ and $\rho_2$, both greater than the fluid density. Such that $\rho < \rho_1 < \rho_2$. Since $(\rho - \rho) > O$ the density differential will result in a disturbed downward thrust oriented vertically with the gravity vector.

In this there are two cases of importance to be considered:
1. The particle velocities are greater than medium velocity-corresponding to the actual physical case during the initial stages of the process, as observed experimentally.
2. Case of pure sedimentation of the particles, as during the final stages of the process.

Case I: (When the particle velocity is greater than fluid velocity). The relative velocity of the lighter particles are $V_{1T} = U + V_1$
and that of the heavier particles are $V_{2T} = U + V_2$
assuming both U and V are positive, directed vertically and assuming initial coincidence of the two classes of particles. Then the particles will travel with these velocities and will be separated by a distance X in time T.

$$X = (V_{1T} - V_{2T}) T = (V_1 - V_2) T \qquad (1)$$

Thus X is a quantity that increases with time but is independent of the fluid velocity. However, the fluid stream velocity by accelerating and, also, aiding the particles in attaining their respective velocities serves to speed up the process - a factor that is not reflected in these simplified equations. Case II: (Case of pure sedimentation). If $F_1$ is the density of the lighter class of particles (but heavier than medium) then the sedimentation velocity is given by $$V_1 = \frac{k(F_1 - \rho) mg}{3\rho w}$$

Similarly, the rate of sedimentation of the heavier particles is given by $$V_2 = \frac{k'(F_2 - \rho) mg'}{3\rho w} \qquad (2)$$

(Where K and K' are the empirical constants to account for the spermatozoa shape) then the relative separational velocity between the two classes of particles if given by $(V_1 - V_2)$ i.e., a quantity that is again dependent on the length of operation but independent of the fluid velocity.

Therefore, it may be inferred that under all cases the eventual separation of the two classes of particles is largely independent of the fluid velocity and is only dependent on the relative densities and the duration of the process operation. The convectional currents serve to aid and accelerate the process of separating the two classes of particles. Therefore, the minute density differential effect is used in conjunction with the convectional counter stream to obtain a purer and optimum separation of the two classes in a shorter time.

From the observational data, it has been noted that the average velocity of the particles in pure sedimentation field at 5°C is 33 m per second, whereas, the average velocity in convection counter stream is 120 m per second. When the height of the column was selected at 18.2 cm the average time taken for pure sedimentation amounts to 15.4 hours in contrast to 24.3 minutes when convection current was used.

Also from the above equation (2), it may be seen that the velocity ratio of the two classes is: 1:3
Where:
P = medium density at 5°C = 1.024
$F_1$ = isopyknic density of lighter class at 5°C = 1.024
$F_2$ = isopyknic density of heavier class at 5°C = 1.034

In other words, once the process of separation has been effected, the sedimentation rate will be three times that of the lighter class. This is the experimentally observed phenomenon. Therefore, the elementary description given above would appear to fit the observed experimental process.

The present invention includes apparatus for producing the above results comprising means adjacent to a sedimentation column for producing the required temperature differential between two portions of the medium contained therein. Additionally, means are provided to determine the extent of accumulation of the two sperm populations at different levels within the sedimentation column both during and after thermal convection counter streaming. This may be achieved by several different means. Small fractions of the medium may be drained to determine the location and concentration of X-sperm and Y-sperm cells or a plurality of small hydrometers may be introduced into the sedimentation column to make the determination by measurement of density. Alternatively, the determination may be made by measurement of conductivity at various points within the column. In the preferred embodiment, the means for determining the location and concentration of the sedimented layers comprises a laser and laser detecting means in combination with means for scanning the laser beam throughout the length of the sedimentation column. Variations in the opacity of the medium to a particular wave length are thus determined, without the necessity of physically disturbing the contents of the sedimentation column in any way. This also facilitates the recording of variations in particle distribution and in the location and concentration of separated layers of X and Y-sperm cells.

Accordingly, it is an object of the present invention to provide a more efficient method for controlling the sex of mammalian offspring.

It is a further object of the present invention to provide a method for obtaining a substantially complete separation of sperm types according to their density.

It is also an object of the present invention to provide a method for substantially complete separation of X-sperm and Y-sperm utilizing both positive and negative buoyant forces.

Another object of the present invention is to provide a method for substantially complete separation of X-sperm and Y-sperm utilizing a thermally produced convection counter stream.

A further object of the present invention is to provide a method of separating sperm according to phenotypical differences related to normal and abnormal genotypes by utilizing differences in their density.

A still further object of the present invention is to provide a method for obtaining a more complete separation of X-sperm and Y-sperm than has heretofore been possible.

Still another object of the present invention is to provide an apparatus for separating X-sperm and Y-sperm by thermally produced convection counter streaming.

Another object of the present invention is to provide an apparatus which utilizes a laser and laser detecting means to determine the distribution and concentration of separated layers of X-sperm and Y-sperm within a sedimentation column.

Additional objects and advantages of the invention will appear from the following description in which the preferred embodiments have been set forth in detail in conjunction with the accompanying drawings in which:

DETAILED DESCRIPTION OF THE PREFERRED EMBODIMENTS

Figure 1:
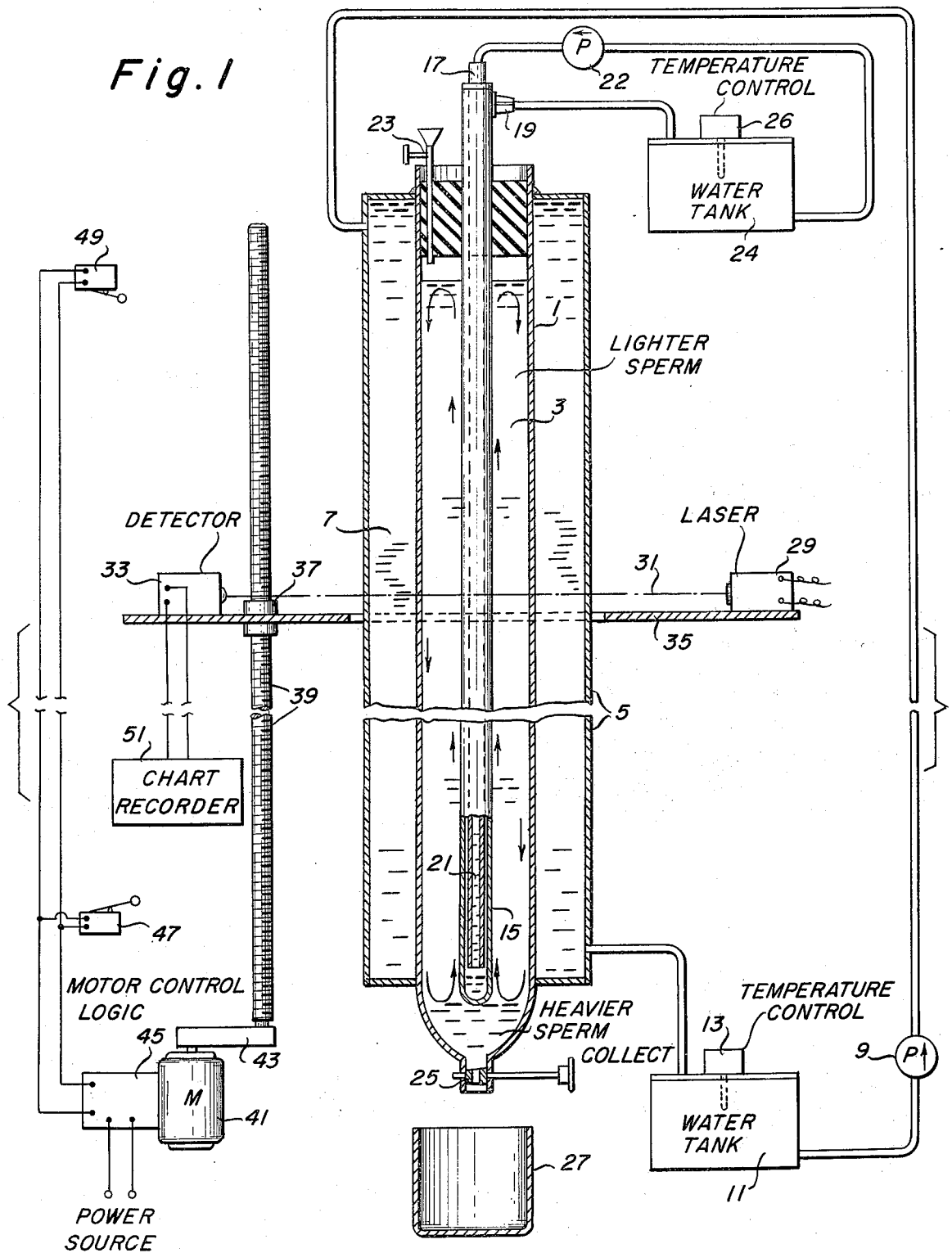
FIG. 1 is a diagram of the apparatus of the present invention.

Shown in FIG. 1 is an illustration of the preferred embodiment of the apparatus used to carry out the method of the present invention. A sedimentation column 1 containing the universal medium 3 with both X-sperm and Y-sperm cells suspended therein is surrounded by a water jacket 5 through which a first water stream 7 of a first temperature is pumped by water pump 9. The water is drawn through water tank 11 where the temperature of the water can be controlled by temperature control means 13. This may comprise a cooling element with precise thermostatic control. Within the medium 3 is shown a second water jacket 15 which is coaxial with sedimentation column 1 and which has inlet 17 and outlet 19. A second stream of water 21 flows through water jacket 15 and may be pumped by means 22 through water tank 24 and its temperature controlled by separate means 26. In the event that the temperature of water stream 7 is the same as water stream 21 the entire medium within the sedimentation column will be at a uniform temperature. If a temperature differential is created between the two water streams, a thermal convection counter stream will result within the medium contained in the sedimentation column. It will be understood of course that other fluid heat exchange mediums may be used in lieu of water.

Inlet means 23 are provided for introducing sperm cells into the medium contained in the sedimentation column and outlet means 25 are provided for withdrawing fractions of sperm of substantially one chromosome type after sedimentation has been completed and collecting them in container 27.

In order to determine the progress of sedimentation as well as the location and concentration of the different types of sperm cells within the medium, means are provided for scanning the length of the sedimentation column and determining the relative opacity at different points therein. These means comprise a laser 29 producing a beam 31 which passes through the medium contained in the sedimentation column and is detected by laser detecting means 33. The laser and detector are both mounted on a platform 35 which is attached to a threaded sleeve member 37. This sleeve member is helically engaged with a threaded jack shaft 39 which is capable of being rotated by a motor 41 through driving means 43. It can be seen that upon rotation of the threaded jack shaft the laser platform 35 can be raised or lowered depending upon the direction of rotation imparted by the motor 41. If a synchronous motor is used it is possible to perform a linear scan along the entire length of sedimentation column 1 in either an upwards or downwards direction. In order to continuously scan the sedimentation column without manually changing the rotational direction of the motor, automatic means are provided for reversing the motor direction which comprise motor control logic 45, switch 47 and switch 49. If platform 35 is scanning upwards the edge of the platform will eventually contact switch 49, upon which, the motor control logic 45 will reverse polarity of the voltage applied to the motor and change the rotational direction of threaded jack shaft 39 thus initiating a scan in the downwards direction. Upon platform 35 subsequently contacting switch 47, motor control logic 45 will again reverse polarity to obtain the original direction of rotation of threaded jack shaft 39 thus initiating a scan of platform 35 in the upwards direction. This sequential scanning can continue for an indefinite period as described. It should be understood that other means of scanning the laser and its associated detector along the length of the sedimentation column could be applied within the scope of the present invention. The apparatus thus described has the capability of efficiently producing the thermal convection counter stream of the method of the present invention as well as to efficiently determine the location and concentration of separated X and Y-sperm cells.

Figure 2:
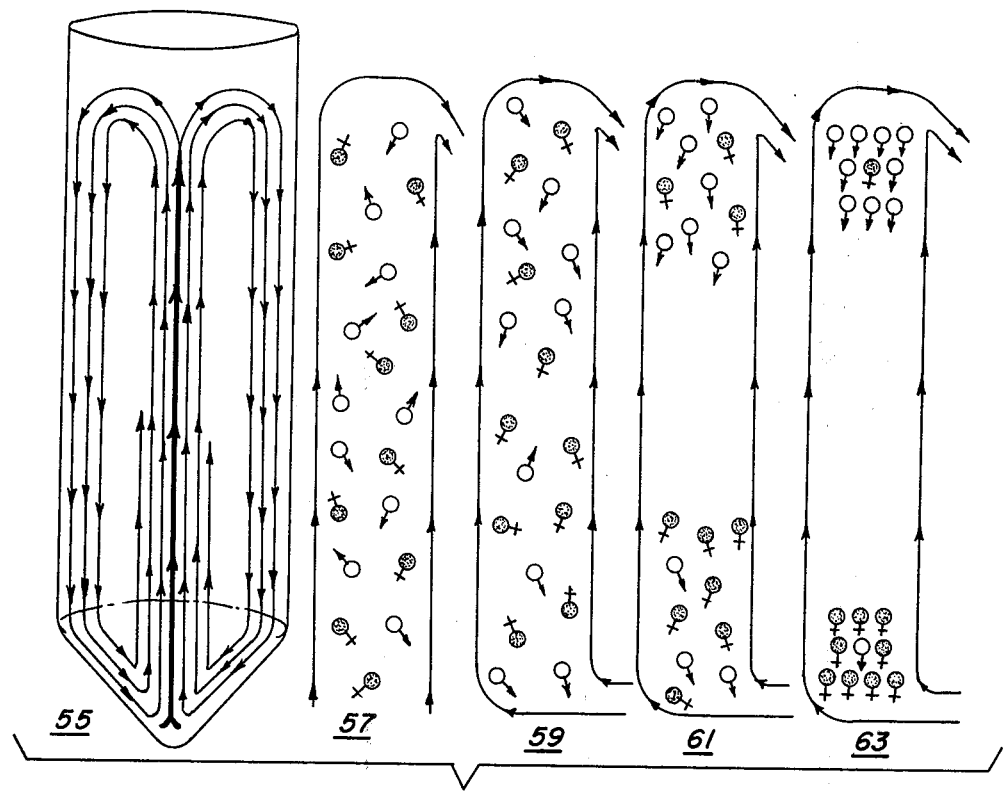
FIG. 2 is a representation of the operation of the method of the present invention.

The method of the present invention as performed by the above described apparatus will now be described with reference to both FIG. 1 and FIG. 2. As discussed previously the preferred medium for use in the sedimentation column in the method of the present invention is the universal medium described in U.S. Pat. No. 3,816,249. This medium comprises a mixture of glycine, α-aminopropionic acid and egg yolk in amounts effective in aqueous solution to extend the life of said semen. The preferred composition of this medium comprises an aqueous solution having a pH in the range of from about 6.0 to 8.0, and containing, by weight, from about 0.01 percent to about 1.0 percent glycine, from about 0.01 percent to about 1.0 percent α-aminopropionic acid, from about 0.1 percent to about 2.0 percent of sodium chloride, potassium chloride or calcium chloride, from about 30 percent to about 55 percent egg yolk, and from about 30 percent to about 70 percent water and is filtered using millipore size 0.2 μ filter. While this medium is preferred, it is possible to practice the method of the invention with other particle free mediums of appropriate composition. Fresh sperm containing equal amounts of X and Y-sperm is collected from the male and mixed immediately with the universal medium at 22°C. The sperm mixture is then diluted further to 30 million cells per ml and checked microscopically for its quality. Only mixtures with excellent grading are used in the separation procedure.

The temperature of the sperm mixture is gradually lowered to 15° centigrade and then introduced into the sedimentation column. The outer water stream 7 is maintained at a temperature of 3.5° centigrade throughout the operation, and water stream 21 contained in coaxial water jacket 15 is maintained at 10° centigrade for one half hour and then brought down to 3.5° centigrade in another half hour by simply cutting off circulation within the coaxial tube. It should be understood that the above temperatures are only representative. In practice, the process may be carried out at any temperature which is sufficiently low to prevent the activity of the sperm cells from interfering with the sedimentation process. The temperature differential created above is also exemplary and any differential which would create sufficient convection counter streaming to facilitate sperm cell separation within a reasonable time would suffice. As previously discussed, the combination of this low temperature and the use of the particle free universal medium play an extremely important role in the invention by immobilizing the sperm so that they effectively become inert particles. This enables the subsequent positive and negative buoyant forces applied to use the 2%–5% difference in density of the two types of sperm to effect a separation. During the period of temperature differential between the central and outer portions of the medium within the sedimentation column a thermal convection counter stream shown diagrammatically at 55 occurs which produces the positive buoyant force in this embodiment. Gravitational sedimentation is the negative buoyant force, and continues when the temperature differential becomes zero and the motion of the ceases. cases. It takes ½ to 8 hours to achieve satisfactory separation beginning with introduction of the sperm mixture into the universal medium contained in the sedimentation column. Throughout this period, distribution of sperm in the sedimentation column at different times shown at 57, 59, 61 and 63 is determined by use of the laser scanning system described above. As the convection separation is stopped, concentration of cells by sedimentation continues dragging both lighter and heavier sperm towards the bottom. By utilizing a chart recorder 51 connected to laser detecting means 33 the distribution of sperm at different times in the separation period can be recorded and observed. When the distribution is considered adequate, outlet means 25 can be opened and the fluid is allowed to drop into container 27 at a rate of approximately 20 drops per minute. The first fractions collected from the sedimentation column will contain the heavier X-chromosome containing sperm and successive fractions will contain less X-chromosome sperm and more Y-chromosome sperm until the final fractions collected will contain substantially all Y-chromosome sperm. Both the lighter Y-chromosome containing fraction and the heavier X-chromosome containing fraction are centrifuged separately to concentrate and purify the products. The purity of the male and female fractions is tested serologically by producing the antibodies as follows: Lighter and heavier fractions from the column are centrifuged repeatedly with fresh medium to concentrate and purify the lighter and heavier sperm. The sediment in the heavier fraction and supernatant in the lighter fraction after repeated centrifuging and washing are considered to hold the most pure forms of the female and male sperm respectively. The subsequent procedure is followed as described in my U.S. Pat. No. 3,692,897, Col. 3, lines 11 through 43 and Col. 5, lines 5 through 55.

An equal amount of universal medium (with about 20% glycerol) is used to dilute the fractions to desired volume and sperm cell number preferably 20 million cells per ml, and the mixture is held at 5 to 8° centigrade for 4 to 6 hours to equilibrate glycerol with the cells. The material is then put into one ml ampules sealed, marked as male, female, or mixture, frozen and stored in liquid nitrogen.

A group of cows was artificially inseminated with female sperm derived by the method of the present invention as described above. After 50 to 60 days gestation 9 of them were slaughtered and the observed fetuses were all of the female sex.

It is feasible by using thermal convection counter streaming sedimentation as described above to avoid most heavy and light sperm considered to form only a small fraction of the sperm population, which carry abnormal chromosomes causing birth defects. This would reduce those cases of Klinefelter's and Turner's syndromes, and autosomal defects caused by nondisjunction and translocation of chromosomes, by rejecting defective heavier and lighter sperm.

From the foregoing it will be apparent that the convection counter streaming sedimentation method of the present invention has utility whenever it is desired to control the sex of mammalian offspring. It is of extreme practical and commercial importance to meet the great demand in increasing herds, cattle and hog herds particularly, by selecting female offspring. It permits the breeder or farmer to have a choice in the sex of the animal. By way of illustration, the dairy farmer and exotic cattle breeder can elect to obtain only female offspring and thereby advantageously breed only milk producing cows rather than bulls or exotic breed bulls rather than cows, as the case may be. As respects to human procreation, it allows normal parents to select or control the sex of offspring to quickly satisfy the desire to have a child of a particular sex, thus providing the opportunity to reduce the total number of children. The observed higher fertility will help in general to achieve better success in artificial insemination. In case of parents carrying defective genes, it would provide them with the opportunity of increasing the chance of having a normal baby by eliminating defective lighter and heavier sperm.

What is claimed is:

1. An apparatus for separating particles of differing densities suspended in a medium comprising:
   a sedimentation column;
   means for introducing into said sedimentation column a medium containing particles of differing densities suspended therein;
   means adjacent to said sedimentation column for producing a temperature differential between two portions of the medium contained in said sedimentation column, whereby a thermal convection counter stream is created; and means for removing desired fractions of said medium from said sedimentation column.

2. An apparatus as recited in claim 1 further comprising means for determining variations in particle distribution within said sedimentation column.

3. An apparatus as recited in claim 2 wherein said means for determining particle distribution comprises:
   a laser the beam of which is directed through the sedimentation column;
   laser detecting means arranged on the opposite side of the sedimentation column to receive the laser beam; and
   means for simultaneously scanning both the laser and the laser detecting means along the length of the sedimentation column, whereby variations in the distribution of particles suspended in the medium therein are determined.

4. An apparatus as recited in claim 3 further comprising means connected to said laser detecting means for recording variations in particle distribution determined by said laser and said laser detecting means.

5. An apparatus as recited in claim 3 wherein said scanning means comprises:
   a motor;
   a stage upon which the laser and laser detecting means are mounted; and
   a threaded jack shaft helically engaged with a portion of the stage and rotatable by the motor.

6. An apparatus as recited in claim 5 wherein said motor is reversible and further comprising means to reverse the rotational direction of said motor in response to the position of said stage.

7. An apparatus as recited in claim 6 wherein said means for reversing the rotational direction of said motor comprises:
   first switching means responsive to a first position of said stage;
   second switching means responsive to a second position of said stage;
   means capable of reversing the direction of said motor, and responsive to said first and second switching means whereby movement of said stage in a first direction is caused by said first switching means and movement in an opposite direction is caused by said second switching means, and whereby said stage is capable of oscillation between said first and second positions.

8. An apparatus as recited in claim 1 wherein said means for producing a temperature differential comprises:
   means for directing at least one heat exchange fluid into contact with a portion of the sedimentation column; and
   means for controlling the temperature of the heat exchange fluid.

9. An apparatus as recited in claim 8 comprising:
   a first water jacket surrounding the sedimentation column and containing a first stream of water;
   a second water jacket within the sedimentation column coaxial therewith and containing a second stream of water; and
   means for separately controlling the temperature of each of said first and second water streams.

* * * * *